(12) United States Patent
Dannoritzer

(10) Patent No.: US 9,814,469 B2
(45) Date of Patent: Nov. 14, 2017

(54) SURGICAL INSTRUMENT

(76) Inventor: Axel Dannoritzer, Baden-Wuertt (DE)

(*) Notice: Subject to any disclaimer, the term of this patent is extended or adjusted under 35 U.S.C. 154(b) by 709 days.

(21) Appl. No.: 13/880,134

(22) PCT Filed: Oct. 25, 2011

(86) PCT No.: PCT/EP2011/005358
§ 371 (c)(1),
(2), (4) Date: Apr. 18, 2013

(87) PCT Pub. No.: WO2012/055530
PCT Pub. Date: May 3, 2012

(65) Prior Publication Data
US 2013/0218162 A1    Aug. 22, 2013

(30) Foreign Application Priority Data
Oct. 25, 2010    (DE) .................. 10 2010 049 244

(51) Int. Cl.
*A61B 17/16* (2006.01)
*B23B 31/00* (2006.01)
(Continued)

(52) U.S. Cl.
CPC ...... *A61B 17/1637* (2013.01); *A61B 17/1613* (2013.01); *A61B 17/1615* (2013.01);
(Continued)

(58) Field of Classification Search
CPC ............ A61B 17/1615; A61B 17/1617; A61B 17/162; A61B 17/1622; A61B 17/1642;
(Continued)

(56) References Cited

U.S. PATENT DOCUMENTS 2,037,307 A    8/1935    Bowman
4,696,308 A    9/1987    Meller et al.
(Continued)

FOREIGN PATENT DOCUMENTS

DE    19803998 A1    8/1999
EP    1 938 757 A1    7/2008
(Continued)

OTHER PUBLICATIONS

International Search Report of the International Searching Authority dated Mar. 30, 2012 for the corresponding international application No. PCT/EP2011/005358 (with English translation).
(Continued)

*Primary Examiner* — Anu Ramana
(74) *Attorney, Agent, or Firm* — Posz Law Group, PLC

(57) ABSTRACT

A tool, in particular for use as a surgical drill, has a main tool body which, in order to be connected to a tool attachment unit, has a fixing unit which is provided to be at least partly unusable after the main tool body has been detached from the tool attachment unit.

The fixing unit has at least one form-fit element, which is provided to accept axial tensile forces in order to axially secure the main tool body to the tool attachment unit. The fixing unit has an assembly direction and a deflection element which points in the assembly direction, and which is provided for movably attaching the form-fit element to the main tool body. It is proposed that the form-fit element and the deflection element have different directions of extension.

7 Claims, 5 Drawing Sheets

(51) Int. Cl.
   *B23B 31/107* (2006.01)
   *A61B 17/00* (2006.01)
   *A61B 90/00* (2016.01)

(52) U.S. Cl.
   CPC .......... *B23B 31/005* (2013.01); *B23B 31/107* (2013.01); *A61B 2017/0023* (2013.01); *A61B 2017/00477* (2013.01); *A61B 2090/0814* (2016.02)

(58) Field of Classification Search
   CPC .............. A61B 17/164; A61B 17/1626; A61B 17/1628
   See application file for complete search history.

(56) References Cited

U.S. PATENT DOCUMENTS

| | | | |
|---|---|---|---|
| 5,330,480 | A | 7/1994 | Meloul et al. |
| 5,741,084 | A | 4/1998 | Del Rio et al. |
| 5,779,708 | A | 7/1998 | Wu |
| 5,871,493 | A | 2/1999 | Sjostrom et al. |
| 7,060,071 | B2 | 6/2006 | Steiger |
| 8,048,078 | B2 | 11/2011 | Reinhard |
| 2002/0165549 | A1 | 11/2002 | Owusu-Akyaw et al. |
| 2003/0097133 | A1* | 5/2003 | Green ................ A61B 17/1617 606/80 |
| 2003/0114839 | A1* | 6/2003 | Looper .......... A61B 17/320016 606/1 |
| 2003/0229351 | A1* | 12/2003 | Tidwell .............. A61B 17/1633 606/80 |
| 2004/0024404 | A1* | 2/2004 | Steiger ............... A61B 17/1617 606/79 |
| 2008/0157488 | A1 | 7/2008 | Kullmer et al. |

FOREIGN PATENT DOCUMENTS

| | | |
|---|---|---|
| EP | 1 943 966 B1 | 7/2008 |
| GB | 2310623 A | 9/1997 |
| WO | 99/38450 | 8/1999 |
| WO | 01/66024 A1 | 9/2001 |

OTHER PUBLICATIONS

Written Opinion of the International Searching Authority dated Mar. 30, 2012 for the corresponding international application No. PCT/EP2011/005358 (with English translation).

German Search Report issued from the German Patent Office dated Aug. 2, 2011 for the corresponding German application No. DE 10 2010 049 244.2 (with partial English translation).

Office Action dated Jun. 9, 2016 issued in corresponding EP patent application No. 11 785 323.4 (and partial English translation).

* cited by examiner

SURGICAL INSTRUMENT

CROSS REFERENCE TO RELATED APPLICATIONS

This application is a U.S. national stage application PCT/EP2011/005358 filed on Oct. 25, 2011, and claims priority to, and incorporates by reference, German patent application No. 10 2010 049 244.2 filed on Oct. 25, 2010.

TECHNICAL FIELD

Prior Art

The invention relates to a tool, in particular for use as a surgical drill.

EP 1 943 966 B1 has already disclosed a tool for use as a surgical drill, having a main tool body which, in order to be connected to a tool connection unit of a drive device, has a fixing unit which is provided to be at least partly unusable after the main tool body has been detached from the tool connection unit.

SUMMARY

The object of the invention is in particular to make available a tool which, with a high degree of strength, in particular in respect of axial forces, can be secured on a tool connection unit. The object is achieved in particular by the features of the independent claims, while further embodiments can be derived from the dependent claims.

The invention relates to a tool, in particular for use as a surgical drill, having a main tool body which, in order to be connected to a tool attachment unit, has a fixing unit which is provided to be at least partly unusable after the main tool body has been detached from the tool connection unit.

It is proposed that the fixing unit has at least one positive form-locking element, which is provided to take up axial tensile forces in order to secure the main tool body axially on the tool connection unit. In this way, axial forces acting on the positive form-locking element can be transferred particularly advantageously to the tool connection unit, as a result of which a particularly firm connection can be achieved for axially securing the tool. The phrase "provided to be at least partly unusable after the tool has been detached" is to be understood in particular as meaning that the fixing unit is designed such that it is no longer usable after the tool has been detached several times at the latest, but preferably after the tool has been detached for the first time, specifically preferably in such a way that renewed axial fixing of the tool is no longer possible. Here, "axial tensile forces" are to be understood in particular as meaning that the positive form-locking element is provided to take up forces that lead to tensile loading of the positive form-locking element and to pass these forces on to the tool connection unit via a positive form-locking. "Tensile forces" are to be understood as forces that in principle would lead to an elongation of the positive form-locking element if the positive form-locking element were made of an elastic material. Moreover, in this context, "provided to secure axially" is to be understood as meaning that the positive form-locking element is provided to ensure that axial forces acting on the tool in the form of a tensile load are transferred to the tool connection unit. "Provided" is to be understood in particular as specially equipped and/or designed.

The fixing unit may have an a mounting direction and a deflection element which points in the mounting direction and which is provided for movable connection of the positive form-locking element to the main tool body. In this way, a particularly advantageous transfer of the tensile forces from the main tool body to the positive form-locking element can take place. The deflection element is in this case preferably provided for a radial deflection of the positive form-locking element. A "mounting direction" is to be understood in particular as a direction that extends parallel to a rotation axis of the tool and that is provided for mounting the tool on the tool connection unit. It is preferably to be understood as a direction which is oriented from a tip of the tool, which tip is provided with drilling teeth, in the direction of an end at which the main tool body has the fixing unit. A "deflection element" is to be understood in particular as an element which is provided for deflecting the positive form-locking element with respect to the main tool body.

According to the disclosure, the positive form-locking element and the deflection element may have different directions of extension. A particularly advantageous fixing unit can be obtained in this way. A "direction of extension" is to be understood in particular as a direction that is oriented along a jacket surface and/or surface of the positive form-locking element or of the deflection element. Different "directions of extension" are to be understood in particular as meaning that a surface of the positive form-locking element and a surface of the deflection element are arranged at an angle to each other.

In a particularly advantageous embodiment, the positive form-locking element and the deflection element are arranged at an acute angle to each other. In this way, it is possible to obtain a particularly advantageous positive form-locking which is provided by the positive form-locking element and which permits safe axial securing of the tool on the tool connection unit. An "acute angle" is to be understood in particular as an angle of less than 90 degrees, with the deflection element and the positive form-locking element preferably having surfaces that enclose the acute angle. Advantageously, the surface of the positive form-locking element is provided as a contact surface for securing the main tool body and particularly advantageously encloses the acute angle with a surface of the deflection element that is oriented in the direction of an interior of the main tool body.

It is also advantageous if the positive form-locking element and the deflection element are formed in one piece. In this way, the positive form-locking element and the deflection element can have a particularly simple design. The deflection element and the positive form-locking element are preferably made in one piece with the main tool body.

It is further proposed that the positive form-locking element is bent at an angle of at least 90 degrees with respect to the deflection element. The positive form-locking element can be produced particularly easily in this way. The phrase "bent at an angle of at least 90 degrees" is to be understood in particular as meaning that the positive form-locking element is produced by a plastic deformation of a one-piece component of which one part, which constitutes the positive form-locking element, is bent at an angle of at least 90 degrees with respect to another part, which constitutes the deflection element.

In a particularly advantageous embodiment, the main tool body has an end with a free cut, which at least constitutes the positive form-locking element. In this way, the positive form-locking element and the deflection element can be produced particularly easily. The positive form-locking element is preferably produced by bending out from a part of the free cut. A "free cut" is to be understood in particular as a part of the main tool body which, by introduction of at least one but preferably two incisions, forms a tongue or tab which is provided to constitute the positive form-locking element and the deflection element. An "end with a free cut" is to be understood in particular as meaning that the free cut is introduced into the main tool body from the direction of the end of the main tool body.

In one refinement, it is proposed that the free cut at least partially forms a recess, which is provided to transfer a torque. In this way, the tool can be designed with a particularly simple structure. In particular, in this way, the recess for transferring torque and the positive form-locking element for axial securing can be made in one piece and thus combined with each other, as a result of which a particularly simple design of the fixing unit is possible.

It is also advantageous if the fixing unit is provided to form a plug connection. A simple fixing unit can be produced in this way.

A tool with a main tool body may be provided to be connected to a tool connection unit so as to rotate therewith and has a fixing unit, which is provided to be at least partly unusable after the main tool body has been detached from the tool connection unit, wherein the fixing unit forms a connection receipt provided for mounting onto the tool connection unit. It is possible in this way to achieve particularly secure fixing of the tool on the tool connection unit. In particular, the fixing unit can thus have a particularly simple design. A "connection receipt" is to be understood in particular as an interior which is enclosed by the main tool body and into which a mount element of the tool connection unit can be introduced, and in which the mount element in the assembled state is arranged for conjoint rotation and is axially secured.

The invention also proposes a tool-fixing device for connection to a tool according to the invention, which tool-fixing device has a tool connection unit, which is provided to drive a tool in a rotational movement about a rotation axis and which has a mount element, which is provided to pass at least partially through a main tool body, and at least one positive form-locking engagement element, which is provided to secure the tool against an axial movement by receiving a positive form-locking element of the tool. In this way, a particularly advantageous and simple tool-fixing device can be made available. A "positive form-locking engagement element" is to be understood as an element that forms a contact surface on which the positive form-locking element of the tool bears.

The positive form-locking engagement element preferably has at least one contact surface for the positive form-locking element, which contact surface is designed as an oblique surface in relation to a cross-sectional surface. In this way, axial tensile forces acting on the positive form-locking element can be converted at least partially into radially acting forces, as a result of which undesired slipping of the positive form-locking element out of the positive form-locking engagement element can advantageously be prevented. A "cross-sectional surface" is to be understood as a surface extending perpendicularly with respect to the rotation axis. In this context, designed as an "oblique surface" is to be understood in particular as meaning that the contact surface of the positive form-locking engagement element encloses an angle of different than zero degrees with the cross-sectional surface. Preferably, the angle is approximately 15 degrees. In the context of angles, "approximately" is to be understood here, and in the text below, as a deviation of at most ±10 degrees, with a deviation of at most ±5 degrees being advantageous, and a deviation of at most ±1 degree being particularly advantageous.

Preferably, the positive form-locking engagement element at least partially forms an undercut. The securing of the positive form-locking element in the positive form-locking engagement element can be obtained particularly simply in this way. An "undercut" is to be understood in particular as meaning that the positive form-locking engagement element has a structure that is designed as an undercut with respect to the radial direction, i.e. that a part of the contact surface is designed as a recess, with respect to the radial direction, in which the positive form-locking element engages.

It is further proposed that the mount element has a recess for forming the positive form-locking engagement element. In this way, the positive form-locking engagement element can have a particularly simple design. Preferably, the mount element and the positive form-locking engagement element are designed in one piece.

In a refinement, it is proposed that the mount element has an oblique surface, which is provided to deflect the positive form-locking element of the tool. In this way, when the tool is mounted onto the tool connection unit, the form-lock element can be introduced particularly easily into the positive form-locking engagement element, as a result of which the tool can be secured on the tool-fixing device in a simple way.

It is also advantageous if the tool-fixing device has a drive connection unit, which is provided for releasable connection to a drive device. In this way, the tool-fixing device can be designed as an adapter, as a result of which existing drive devices can still be used. A "drive device" is to be understood as a device with at least one drive motor, which is provided to impart a rotational movement to the tool.

The invention moreover proposes a system with a tool according to the invention and with a tool-fixing device according to the invention.

BRIEF DESCRIPTION OF THE DRAWINGS

Further advantages will become clear from the following description of the drawing. The figures depict an illustrative embodiment of the invention. The figures, the description and the claims contain numerous features in combination. A person skilled in the art will also consider the features individually, where appropriate, and combine them to form meaningful further combinations.

DETAILED DESCRIPTION

Figure 1:
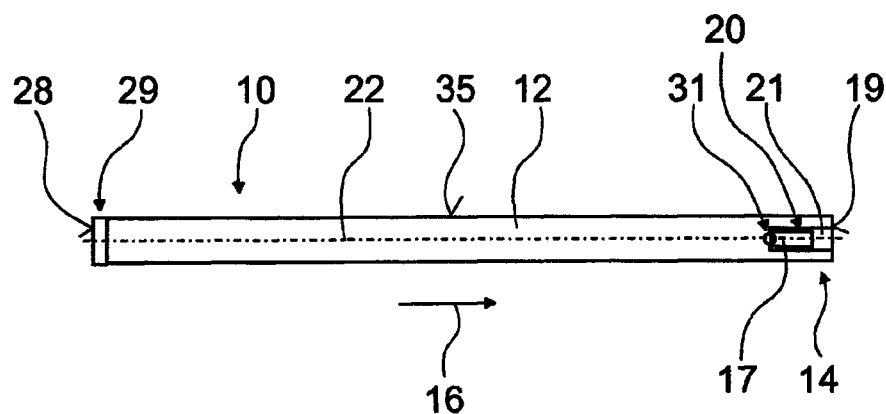
FIG. 1 is a view of a tool according to the invention in a view from above.
Figure 2:
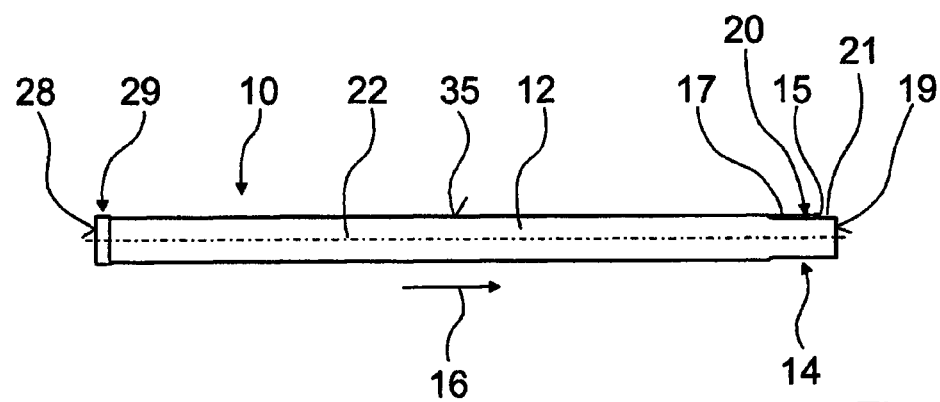
FIG. 2 is a view of the tool from FIG. 1 in a side view.
Figure 3:
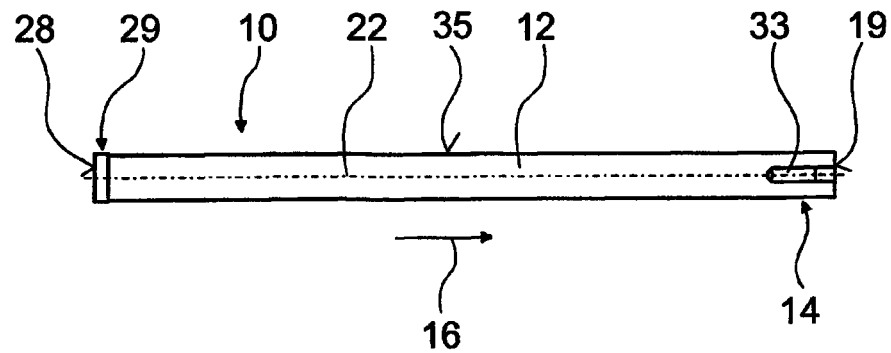
FIG. 3 is a view of the tool according to the invention in a view from below.
Figure 4:
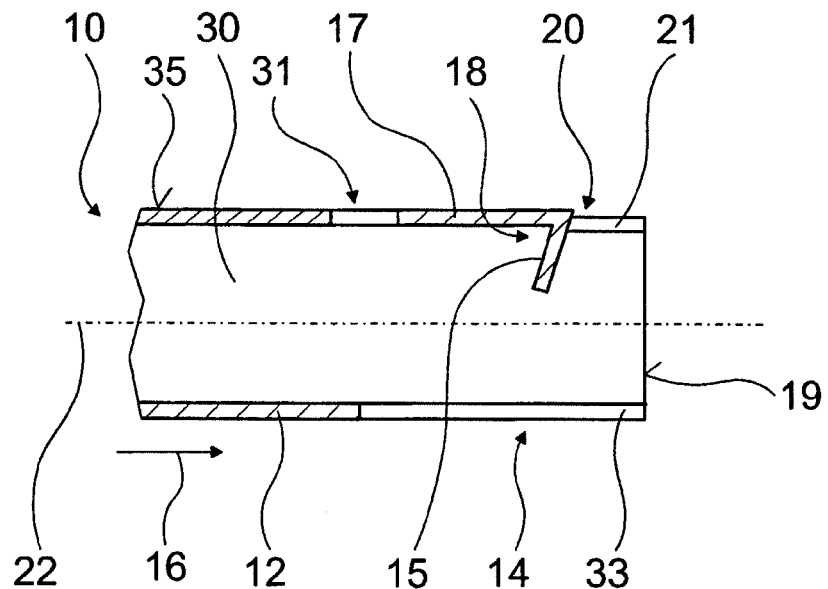
FIG. 4 is a cross sectional view through a fixing unit of the tool.
Figure 5:
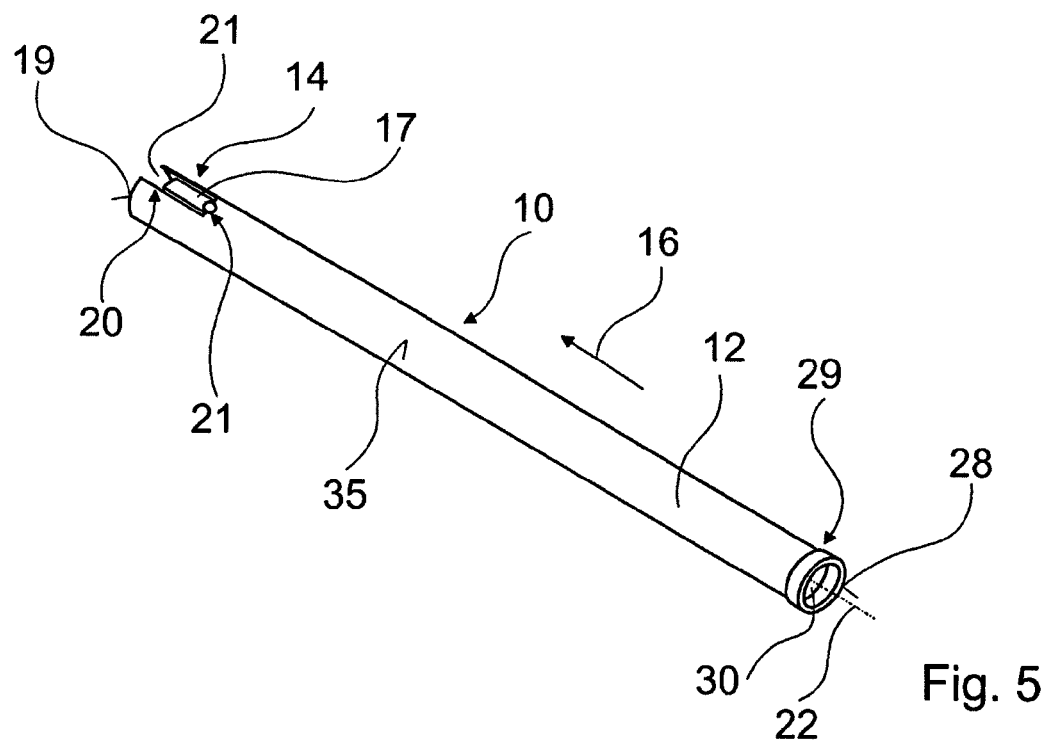
FIG. 5 is a perspective view of the tool.

A tool 10 according to the invention is shown in FIGS. 1 to 5. The tool 10 is provided for drilling holes in bone, particularly for removing drilled cores from bone. The tool 10 comprises a main tool body 12, which can be driven about a rotation axis 22.

The main tool body 12 has a tip 28, which is provided for drilling the hole in the bone, and an end 19, which is provided for connection to a drive device (not shown) for rotation therewith. The tool 10 thus forms a surgical instrument.

At its tip 28, the main tool body 12 has drilling teeth 29 forming a grinding or cutting device by means of which the hole can be drilled in bone. To form the drilling teeth 29, diamond elements are mounted on the tip 28 of the main tool body 12. The diamond elements are produced from artificial diamonds. In order to remove drilled cores, the main tool body 12 is designed with a tubular shape at least at the tip 28.

At its end 19, the main tool body 12 has a fixing unit 14. The fixing unit 14 is provided for connecting the main tool body 12 to a tool connection unit 13 of the drive device so as to rotate therewith while being secured against axial movement. The fixing unit 14 forms part of a plug connection. By means of the fixing unit 14, the main tool body 12 is connectable to the tool connection unit 13 by a linear movement along the rotation axis 22. The main tool body 12 is also designed with a tubular shape at the end 19. It can thus be mounted onto the tool connection unit 13. A direction of the linear movement here defines a mounting direction 16 for the fixing unit 14. The mounting direction 16 is from the tip 28 to the end 19. The movement by which the main tool body 12 is connectable to the tool connection unit 13 is oriented along this mounting direction 16.

The tool 10 is provided as a disposable tool. To make it difficult or impossible for the tool 10 to be used more than once, the fixing unit 14 is designed such that it is at least partly unusable after the main tool body 12 has been detached from the tool connection unit 13. Upon detachment of the main tool body 12 from the tool connection unit 13, the fixing unit 14 is deformed or altered in such a way that it is no longer possible for the main tool body 12 to be fixed anew on the tool connection unit 13 so as to rotate therewith while being axially secured.

To axially secure the main tool body 12, the fixing unit 14 comprises a positive form-locking element 15, which is provided to take up axial tensile forces. The positive form-locking element 15 is designed as a hook which, in a state of assembly, engages in a corresponding positive form-locking engagement element 24 of the tool connection unit 13. The positive form-locking element 15 secures the main tool body 12 against the axial movement. The tensile forces, which are taken up by the positive form-locking element 15 in order to axially secure the main tool body 12 on the tool connection unit 13, are forces that act counter to the mounting direction 16.

In order to attach the positive form-locking element 15 to the main tool body 12, the fixing unit 14 has a deflection element 17 via which the positive form-locking element 15 is connected to the main tool body 12. The deflection element 17 comprises a first end, which is connected to the main tool body 12, and a second end, which is connected to the positive form-locking element 15. Starting from the end connected to the main tool body 12, the deflection element 17 extends in the direction of the positive form-locking element 15.

The deflection element 17 is provided for movably connecting the positive form-locking element 15 to the main tool body 12. The positive form-locking element 15 and the deflection element 17 form part of a locking unit, which is provided for axially securing the main tool body 12 on the tool connection unit 13. Starting from the end of the deflection element 17 connected to the main tool body 12, the deflection element 17 points in the mounting direction 16, i.e. in the direction of the end 19. The deflection element 17 is designed in the form of a tab or tongue that is oriented in the direction of the end 19 of the main tool body 12.

The positive form-locking element 15 and the deflection element 17 have different directions of extension. The deflection element 17 extends substantially parallel to the rotation axis 22. In a delivery state, an angle between the direction of extension of the deflection element 17 and the rotation axis 22 is approximately zero degrees. The positive form-locking element 15 extends substantially perpendicularly with respect to the rotation axis 22. An angle 18 between the direction of extension of the positive form-locking element 15 in the delivery state and the main rotation axis 22 is approximately 75 degrees. The angle 18 at which the positive form-locking element 15 and the deflection element 17 are arranged in relation to each other is therefore configured as an acute angle. The deflection element 17 points in the mounting direction 16. The positive form-locking element 15 points counter to the mounting direction 16.

The positive form-locking element 15, the deflection element 17 and the main tool body 12 are formed in one piece. The entire main tool body 12 is designed with a tubular shape. At its end 19, the main tool body 12 has a free cut 20, which forms the deflection element 17 and the positive form-locking element 15. The free cut 20 is formed by two incisions which extend substantially parallel to each other and which are introduced into the main tool body 12 from the direction of the end 19. The form-locking element 15 is formed by bending part of the free cut 20. The positive form-locking element 15 is in this case bent inward. It thus protrudes into an interior 30 which is enclosed by the main tool body 12. The deflection element 17 is designed as that part of the free cut 20 that remains substantially unchanged.

In an area in which the deflection element 17 is connected to the main tool body 12, the tool 10 has a material weakening 31. The material weakening 31 forms a predetermined breaking point. In the illustrative embodiment shown, the material weakening 31 is formed by a hole arranged between the two incisions that form the free cut 20. However, it is also possible in principle to design the free cut 20 by means of incisions tapering toward each other, as a result of which a material weakening 31 can likewise be achieved. Moreover, it is also conceivable that the main tool body 12, in the area in which the main tool body 12 merges into the deflection element 17, has a wall thickness that is reduced compared to the rest of the main tool body 12. The reduced wall thickness can be obtained, for example, by introducing a groove in this area, which groove is advantageously formed by punching.

By bending the positive form-locking element 15, the free cut 20 forms a recess 21 that extends as far as the end 19 of the main tool body 12. A corresponding drive element 32 of the tool connection unit 13 can engage in the recess 21, as a result of which a part of the free cut 20 is provided for torque transfer.

The main tool body 12 further comprises a recess 33, which is provided only for torque transfer. The recess 33 is arranged axially overlapping the free cut 20. With respect to the rotation axis 22, the further recess 33 is arranged lying opposite the free cut 20.

Figure 6:
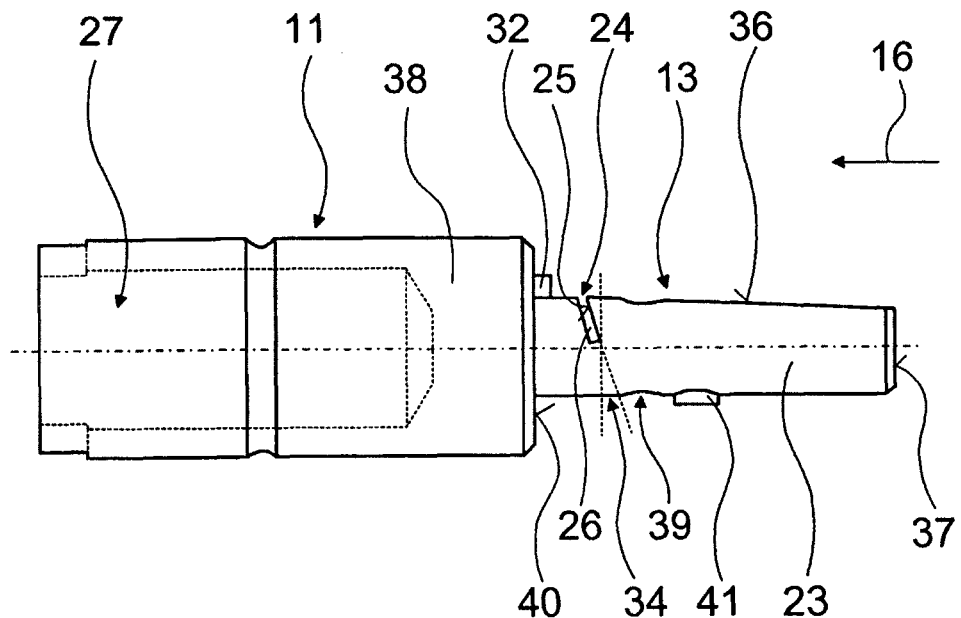
FIG. 6 is a side view of a tool-fixing device according to the invention.
Figure 7:
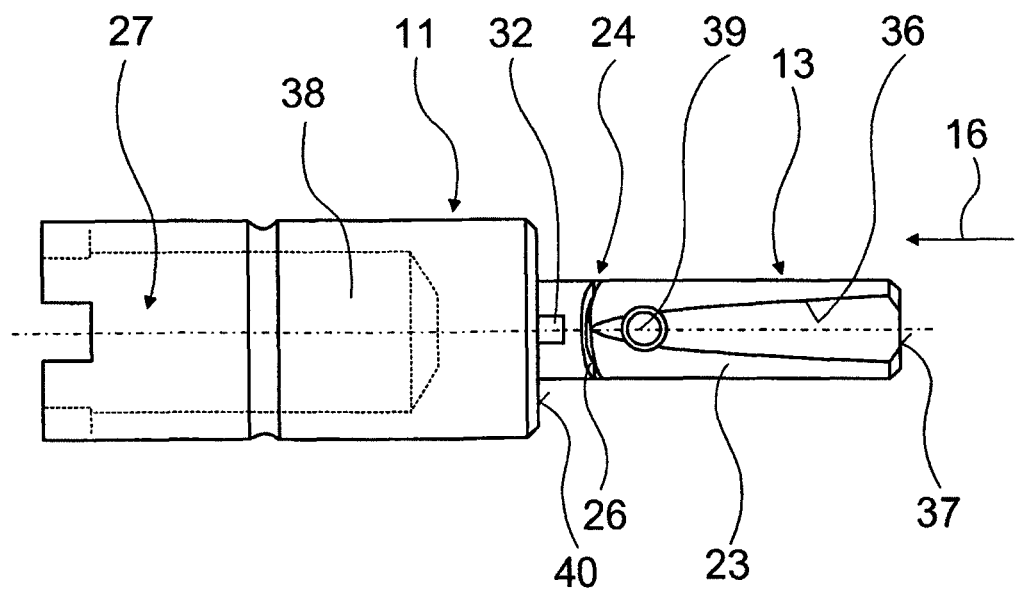
FIG. 7 is a view of the tool-fixing device in a view from above.
Figure 8:
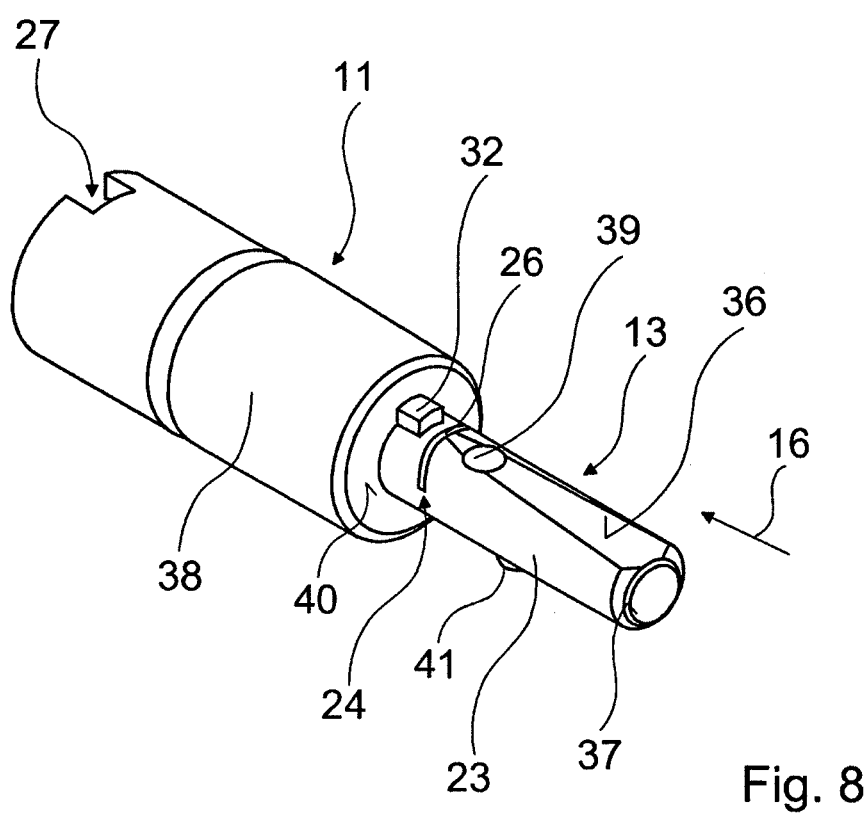
FIG. 8 is a perspective view of the tool-fixing device.

FIGS. 6 to 8 show a tool-fixing device 11 with the tool connection unit 13 for connecting the tool 10 such that it rotates with the tool connection unit 13 while being axially secured. The tool connection unit 13 comprises a main body 38 and a mount element 23 which is connected to the main body 38 and which, in an assembled state, passes partially through the main tool body 12 of the tool 10. The mount element 23 and the main body 38 are formed in one piece. The tool connection unit 13 further comprises the positive form-locking engagement element 24, which is provided for receiving the positive form-locking element 15 of the main tool body 12.

The mount element 23 has a substantially cylindrical basic shape. The mount element 23 has an external diameter that is at least slightly smaller than an internal diameter of the main tool body 12. In order to produce the positive form-locking engagement element 24, which is provided for the positive form-locking element 15 of the fixing unit 14 of the main tool body 12, the mount element 23 comprises a recess 26. The recess 26 is designed in the form of a slit. The mount element 23 itself is designed as a hollow body element.

The positive form-locking engagement element 24 forms a contact surface 25 for the positive form-locking element 15. The contact surface 25 is designed as an oblique surface in relation to a cross-sectional surface, i.e. a surface that extends perpendicularly with respect to the rotation axis 22. The contact surface 25 is tilted at an angle 34 of approximately 15 degrees with respect to the cross-sectional surface. Opposite the contact surface 25, the positive form-locking engagement element 24 has a second surface which, when the recess 26 is designed in the form of a slit, extends substantially parallel to the contact surface 25. In principle, the recess 26 can also be designed in the shape of a wedge, as a result of which the contact surface 25 and the opposite surface would be at an angle to each other.

The positive form-locking engagement element 24 forms an undercut with respect to a radial direction, i.e. a direction perpendicular to the rotation axis 22. The contact surface 25 is designed as a partial cut through the mount element 23. The contact surface 25 is thus designed as a surface in the shape of part of a circle. It comprises a bottom line, which extends through the mount element 23, and a jacket line, which is defined by a jacket surface 35 of the mount element 23.

The bottom line of the contact surface 25 extends perpendicularly with respect to the rotation axis 22. Starting from the bottom line, the height lines of the contact surface 25 enclose, with the rotation axis 22, an angle different than 90 degrees. Starting from the bottom line, the contact surface 25 is thus inclined in the direction of the mounting direction 16, wherein the bottom line can be regarded as an axis for the inclination of the contact surface 25. Thus, seen from the outside in the radial direction, it forms an undercut in which the positive form-locking element 15 engages in the assembled state. A tensile force that is taken up by the contact surface 25, and that can be transferred via the positive form-locking element 15, produces a holding force that makes it impossible or at least difficult for the positive form-locking element 15 to slip out of the positive form-locking engagement element 24.

To make it easier for the tool 10 to be mounted on, the mount element 23 of the tool connection unit 13 has an oblique surface 36, which is provided for deflecting the positive form-locking element 15 in relation to the main tool body 12 when the tool 10 is mounted on the tool connection unit 13. To form the oblique surface 36, the mount element 23 has, within a partial area, a diameter that increases continuously in the direction of the main body 38 starting from a tip 37. The oblique surface 36 is in this case arranged flush with the positive form-locking engagement element 24 in relation to the rotation axis 22.

To release the tool 10 from the tool connection unit 13, the mount element 23 has a recess 39. The recess 39 passes completely through the mount element 23 along a direction that is oriented perpendicularly with respect to the rotation axis 22. The recess 39 is in this case introduced into the mount element 23 in the area of the oblique surface 36.

In order to limit the depth to which the tool 10 can be mounted on, the tool-fixing device 11 has an axial bedstop 40. The main body 38 forms an bedstop surface for the axial bedstop 40. The bedstop 40 and the mount element 23 are formed in one piece with the main body 38. To form the bedstop 40, the tool-fixing device 11 has an increased diameter in an area adjoining the mount element 23 in the axial direction.

In order to transfer torques, the tool connection unit 13 comprises the drive element 32, which is provided for engagement in the recess 21 formed on the main tool body 12 by the free cut 20. The tool connection unit 13 further comprises a drive element 41, which is provided for engagement in the recess 33. The drive element 32 is arranged on the same side of the mount element 23 as the positive form-locking engagement element 24. The drive element 41 is arranged on the side of the mount element 23 that lies opposite the positive form-locking engagement element 24 in relation to the rotation axis 22. The drive element 32 is formed in one piece with the main body 38. The drive element 41 is designed as an additionally inserted pin connected rigidly to the mount element 23. In principle, however, any desired configurations are conceivable for the drive elements 32, 41. In particular, it is also possible to omit the drive element 32 and the corresponding recess 33 on the main tool body 12.

The tool-fixing device 11 further comprises a drive connection unit 27, which is designed for releasable connection to the drive device. The tool connection unit 13 and the drive connection unit 27 are aligned coaxially with each other. The tool connection unit 13 and the drive connection unit 27 have different designs. The tool-fixing device 11 is thus designed as an adapter, which is provided for establishing a connection between a drive of the drive device and the tool 10.

To fix the tool 10 on the tool-fixing device 11, the main tool body 12 of the tool 10 is first of all mounted onto the mount element 23 of the tool connection unit 13. The positive form-locking element 15 is deflected by the linear movement along the mounting direction 16, as a result of which the deflection element 17, which is initially arranged almost parallel to the jacket surface 35 of the main tool body 12, is also deflected outward. As soon as the positive form-locking element 15 is axially to the height of the positive form-locking engagement element 24, the positive form-locking element 15 engages in the positive form-locking engagement element 24. By means of a tensile force applied to the tool 10, the positive form-locking element 15 is brought into complete engagement with the positive form-locking engagement element 24.

To release the tool 10, the deflection element 17 is pushed upward and outward using a suitable tool, which is guided through the recess 33 in the main tool body 12 and through the recess 39 in the mount element 23. The upward push causes a plastic deformation in the area of the material weakening 31, as a result of which the connection between the main tool body 12 and the deflection element 17 is weakened. After only a few uses, but preferably after just one use, this connection is so weakened that it breaks, as a result of which the tool 10 can then no longer be fixed axially on the tool-fixing device 11.

Figure 9:
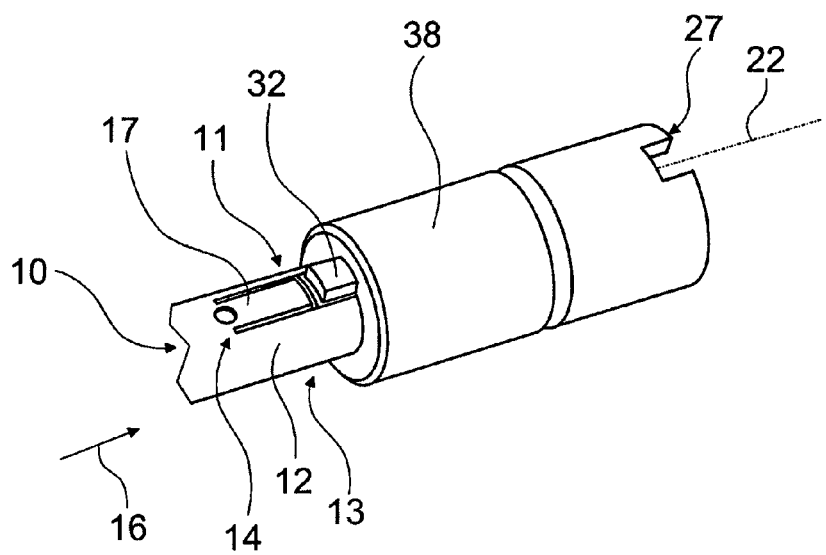
FIG. 9 is a view of a system with the tool from FIGS. 1 to 5 and the tool-fixing device in an assembled state.
Figure 10:
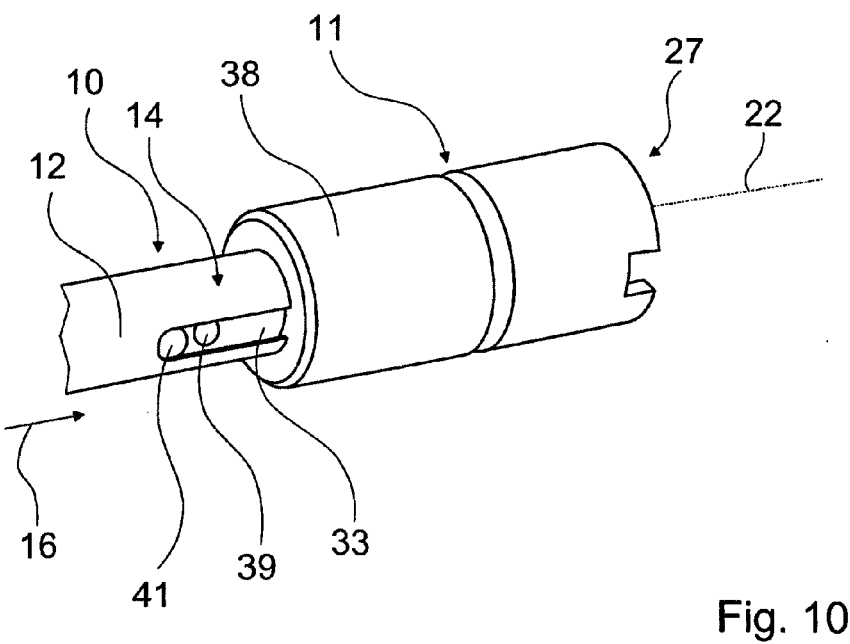
FIG. 10 is a view of the system in a view from below.

FIGS. 9 and 10 show a system composed of the tool-fixing device 11 and of the tool 10. In the assembled state, the positive form-locking element 15 of the tool 10 engages in the positive form-locking engagement element 24 of the tool connection unit 13. In the assembled state, the deflection element 17 again extends almost parallel to the jacket surface 35 of the main tool body 12. Tensile forces acting on the tool 10 are transferred to the tool connection unit 13 via the deflection element 17 and the positive form-locking element 15. Tensile forces likewise act on the deflection element 17 and the positive form-locking element 15. A surface of the positive form-locking element 15, which surface is directed toward the drilling teeth 29 of the main tool body 12, and the contact surface 25 of the mount element 23, which contact surface 25 is directed toward the bedstop 40, form the locking connection for axially securing the tool 10.

In an alternative embodiment not shown in detail, the tool-fixing device 11 comprises a mechanism which is provided for inactivating the at least one drive element 32, 41 for rotation connection of the main tool body 12. When the mechanism is actuated, the corresponding drive element 32, 41 becomes recessed within the mount element 23, as a result of which the main tool body 12 can be turned on the mount element 23. This turning has the effect that the positive form-locking element 15 is rotated sideways out of the positive form-locking engagement element 24, as a result of which the deflection element 17 is deflected outward at the same time. The deflection has the effect that the material weakening 31 is likewise so weakened that the deflection element 17 with the positive form-locking element 15 breaks off immediately or upon renewed insertion of the tool 10. After the tool 10 has been released from the tool-fixing device 11, the fixing unit 14 of the main tool body 12 is thus unusable.

The invention claimed is:

1. A tool for use as a surgical drill, comprising:
   a main tool body that includes a first axial end and a second axial end, a fixing unit located at the first axial end and configured to attach the main tool body to a tool connection unit of a drive device, and a drill device located at the second axial end;
   a locking unit that is located in the fixing unit, and that includes a locking element to secure the main tool body against axial movement, and a deflection element that extends substantially parallel to the rotation axis of the main tool body to movably connect the locking element to the main tool body; and
   a drive device re-attachment prevention portion located between the main tool body and the deflection element,
   the deflection element is configured to break the drive device re-attachment prevention portion upon detachment of the fixing unit from the drive device, wherein
   an angle between a direction of extension of the locking element and a rotation axis of the main tool body is configured as an acute angle.

2. The tool recited in claim 1, wherein the locking element and the deflection element are formed as a single piece.

3. The tool recited in claim 1, wherein the fixing unit is configured to plug onto a plug-on element of the tool connection unit of the drive device.

4. The tool recited in claim 1, wherein the fixing unit comprises an attachment seat that plugs onto a plug-on element of the tool connection unit of the drive device.

5. The tool recited in claim 1, wherein
   the tool is part of a tool fixing device, and the tool fixing device includes the tool connection unit, which is provided to drive the tool about a rotation axis, a mount element, which is provided to pass at least partially through the main tool body, and at least one form-locking engagement element, which is provided to receive the locking element of the tool to secure the tool against axial movement,
   the form-locking engagement element has at least one contact face for the locking element, wherein
   the at least one contact face comprises an oblique face enclosing an angle different than zero degrees with a cross-sectional plane that extends perpendicularly with respect to the rotation axis of the main tool body.

6. The tool recited in claim 5, wherein the form-locking engagement element comprises a recess of the mount element for engaging the locking element.

7. The tool recited in claim 5, further comprising a drive attachment unit provided for releasable attachment to the drive device.

* * * * *